United States Patent [19]

Rutner et al.

[11] 4,256,724

[45] Mar. 17, 1981

[54] METHOD FOR NON-COVALENT COATING OF ANTIBODIES ON SOLID SUBSTRATES

[75] Inventors: Herman Rutner, Hackensack, N.J.; Thomas F. Dodd, Bronx, N.Y.

[73] Assignee: Becton, Dickinson and Company, Paramus, N.J.

[21] Appl. No.: 879,801

[22] Filed: Feb. 21, 1978

[51] Int. Cl.$^2$ .................. G01N 33/16; B01J 1/22; A61K 39/00
[52] U.S. Cl. .................. 424/1; 23/230 B; 422/68; 424/12; 424/16
[58] Field of Search .................. 424/1, 1.5, 12, 16; 23/230 B

[56] References Cited

U.S. PATENT DOCUMENTS

| | | | |
|---|---|---|---|
| 3,951,748 | 4/1976 | Devlin | 195/103.5 |
| 4,017,597 | 4/1977 | Reynolds | 424/1.5 |

Primary Examiner—Benjamin R. Padgett
Assistant Examiner—Christine M. Nucker
Attorney, Agent, or Firm—Louis E. Marn; Elliot M. Olstein

[57] ABSTRACT

Antibodies to lipophilic haptens and antigens, such as the antibodies of bile acids are non-covalently coated on a solid substrate for use in solid phase immunoassays by including in the antibody coating solution an inorganic salt, such as ammonium sulfate, to increase the ionic strength of the solution.

31 Claims, No Drawings

METHOD FOR NON-COVALENT COATING OF ANTIBODIES ON SOLID SUBSTRATES

This invention relates to the assay of antigens and haptens, and more particularly to articles suitable for the solid phase assay of antigens and haptens and to the preparation thereof.

Antigens and haptens can be assayed by a method which involves competition between the analyte and a labeled form thereof for a limited number of antibody sites. Thus, for example, when a known quantity of a labeled form of the hapten or antigen, a known quantity of an antibody for the antigen or hapten, and a sample containing the hapten or antigen are combined and incubated, the percentage of the labeled form of the antigen or hapten bound to the antibody will vary inversely with the quantity of antigen or hapten in the sample. After separating the antibody bound antigen or hapten from the antigen or hapten not bound to the antibody or remaining in solution, the amount of labeled component in either or both fractions may be compared with a standard curve to determine the quantity of antigen or hapten which was present in the sample.

In order to facilitate separation of the antibody from the sample, in many cases, the antibody is bound either covalently or non-covalently to a solid phase; e.g., in the form of a tube, insoluble particles or the like, whereby the antibody, including bound hapten or antigen, can be easily separated from a liquid phase for making a determination as to the quantity of labeled hapten or antigen which is either bound to the antibody or remains free in the liquid phase.

It has been found that some antibodies cannot be readily non-covalently coated on a unmodified solid substrate, and as a result, prior chemical modification and/or activation of the substrate surface is required.

In accordance with the present invention, it has been found that antibodies to lipophilic antigens and antibodies to lipophilic haptens can be coated on unmodified solid substrates by including in the antibody solution a salt (one or more such salts) to increase the ionic strength of the solution. Accordingly, such antibodies can be coated on a solid substrate by contacting the solid substrate with a solution containing such antibodies and an inorganic salt to increase the ionic strength of the solution, whereby upon subsequent removal of the solution, there is provided a solid substrate coated with the antibody.

The antibodies which are coated on the solid substrate are antibodies to lipophilic haptens or antigens. As representative examples of such lipophilic haptens or antigens, there may be mentioned; bile acids in conjugated and unconjugated forms as well as the corresponding sulfate esters; steroids such as testosterone, androsterone, progesterone, estrone, estradiol, estriol, deoxycorticosterone, cortisol, cortisone, aldosterone, etc, cardiotonic glycosides such as digoxin, digitoxin, ouabain, deslanoside and their aglycones; hormones such as $T_4$ and $T_3$; vitamins such as B, C, E, K and folic acid; etc.

The antibodies of such lipophilic antigens or haptens are known in the art, and can be produced by procedures known in the art. Thus, as known in the art, such antibodies are produced by injecting the antigen, or the hapten coupled to a suitable carrier to produce an immunogen, into the bloodstream of a host animal. The manner of producing antibodies to haptens and antigens is known in the art and no further details in this respect are needed for complete understanding of the present invention.

The solid substrate on which the antibody is coated may be any one of a wide variety of solid materials. As known in the art, such materials include suitable polymers, such as polystyrene, polyethylene, polypropylene, polytetrafluoroethylene, polyamides, polyacrylamides, polyvinylchloride; etc.; glass; bacterial cells; ion exchange resins; etc. Such solid carriers are known in the art and no further details in this respect are deemed necessary for a full understanding of the invention.

The salt which is added to the antibody solution to increase the ionic strength thereof is a soluble salt which does not adversely affect the antibody. The salt, preferably an inorganic salt, is selected and employed in an amount to provide a solution having an ionic strength of at least 0.5 and preferably at least 1.0. In general, the ionic strength of the solution does not exceed 10, and most generally does not exceed 5. The ionic strength of a solution is calculated or defined as follows:

$$\text{Ionic strength} = \tfrac{1}{2}\Sigma M i \, Z^2 i$$

wherein
M i = molarity of the ion
ZI = charge of the ion

Thus, the ionic strength is the sum of the noted product for each ion present in the solution, divided by 2.

As representative examples of the inorganic salts soluble in the coating solution which are employed to increase the ionic strength of the solution, there may be mentioned: water soluble salts of alkali metals and ammonium, such as halides; sulfates, nitrates, phosphates, carbonates, bicarbonates, etc; water soluble alkaline earth metal salts, such as nitrates, halides, etc; and the like.

An aqueous antibody solution, containing the inorganic salt, may also include other components conventionally employed for coating of antibodies on a solid substrate, such as a suitable buffer and preservatives. The use of such buffers, and other components is known in the art, and no details in this respect are deemed necessary for a complete understanding of the present invention.

The antibody may be coated onto the substrate by general procedures known in the art. In general, the coating can be effected at room temperatures, although higher or lower temperatures could be employed. Similarly, the antibody titer of the dilute antibody solution is at a value to provide the desired antibody coating. In general, the antibody titer is in the order of from $1:10^3$ to $1:10^6$.

The solid substrate may be in the form of a sheet film, solid particles, tubing, cups, or test tubes, with test tubes being preferred.

The most preferred form of the test tube is a plastic test tube, such as a test tube formed from polystyrene or polypropylene.

The antibody coated on the solid substrate may be employed in a solid phase immunoassay as known in the art. In such assays, antibody coated on the solid substrate is contacted with a sample containing the hapten or antigen and a known quantity of the labeled form of the hapten or antigen. The hapten or antigen may be radiolabeled; e.g., with tritium or radioiodine; enzyme labeled; fluorescent labeled, etc. After separation of the sample from the antibody coated on the solid substrate, the amount of the labeled form of the antigen or hapten bound to the antibody coated substrate and/or sample is determined and the amount of antigen or hapten in the sample is determined from a standard curve. The general techniques for such assays are known in the art, and no further details in this respect are deemed necessary for complete understanding of the present invention.

The present invention is particularly applicable to the production of a conjugated bile acid antibody coated solid substrate, which can then be employed in a solid phase immunoassay for conjugated bile acid. Heretofore, the immunoassay for conjugated bile acid was effected in the liquid phase, or with antibody covalently attached to a support.

Antibody to conjugated bile acid, produced by techniques generally known in the art, is dissolved in water, which is preferably buffered to a pH in the order of from about 5.0 to 10.0. The antibody titer of the solution is generally in the order of 1:$10^3$ to 1:$10^6$, and preferably from 1:$10^4$ to 1:$10^5$. The ionic strength of the solution is increased by the addition of an inorganic salt to provide a solution having an ionic strength of from 0.5 to 10, and preferably from 3 to 6. The inorganic salt is preferably ammonium, potassium or sodium sulfate, which can be employed alone or in admixture with another salt, e.g., sodium chloride.

The antibody is coated on a solid substrate by contacting the substrate with the antibody solution. The substrate is preferably a plastic test tube, with a polystyrene test tube being most preferred. The conjugated bile acid antibody coated tube may then be employed in a radioimmunoassay for conjugated bile acid, with the technique generally corresponding to that employed for a liquid phase immunoassay, except that there is no necessity for adding an additional component for separating the bound and free portions. The tracer may be a radiolabeled form of the conjugated bile acid, preferably a radioiodinated form, although a tritium labeled form of the conjugated bile acid may also be employed. Thus, for example, the following is an illustrative procedure:

To 0.1 ml of diluted serum in antibody coated disposable 12×75 mm polystyrene (Elkay Products, Inc. Worcester, Mass.) is added, cholylglycyl histamine -$^{125}$ I in an amount sufficient to produce 35-45% binding of the radioiodinated antigen in the absence of endogenous conjugated bile acids. The mixture is incubated for 1 hour at 37° C. Competition between the radioiodinated and the unlabeled antigen occurs for binding sites on the antibody coated to the walls of the tube, and determines the amount of radioiodinated antigen-antibody complex present on the surface of the tube at equilibrium. Separation of the antigen-antibody complex, bound to the surface of the tube is determined by counting the tube in a gamma counter. The tracer can be prepared as disclosed by J. G. Spenney et al "An $^{125}$I Radioimmunoassay for Primary Conjugated Bile Salts" Gastroenterology Vol. 72 p. 305-311 (1977).

The present invention will be further described with respect to the following examples; however, such examples do not limit the overall scope of the invention.

EXAMPLE 1

Antiserum specific for conjugated bile acids (titer 1:400,000) was diluted 1:5000 in 0.3 M glycine and 0.10 ml aliquots were dispensed into 10×75 mm polystyrene or polypropylene test tubes. A second aliquot (0.90 ml) of coating solution containing 22% ammonium sulfate and 2.7% sodium chloride was added either concurrently or sequentially. The mixture was incubated overnight at 4° C. and aspirated. The tubes were treated with 1.0 ml post-coat solution (0.1% polyethylene glycol, molecular wt. 6000 (PEG 6000) in 0.01 M pH 7.4 potassium phosphate). Trace Binding=40%. Trace binding is the ratio of the amount of labeled antigen bound to the coated antiserum to the total amount added to the tube.

Employing the exact same procedure, except for the addition of the coating solution, trace binding was 3-9% indicating that the antiserum was not effectively coated on the tube when not using the salt in accordance with the invention.

EXAMPLE 2

Antiserum specific for conjugated bile acids (1:400,000 titer) was diluted to 1:5000 in 0.3 M glycine and 0.10 ml aliquots were dispensed into 12×75 mm polystyrene test tubes. A second aliquot (0.90 ml) of coating solution containing sodium carbonate-bicarbonate solution at pH 9.6 0.5 M, was added. The mixture was incubated overnight at 4° and aspirated. The tubes were treated with 1 ml postcoat solution (0.1% PEG 6000 in 0.01 M pH 7.4 potassium phosphate). Trace Binding=25%.

EXAMPLE 3

Example 2 was repeated, except second aliquot of coating solution contains 10% sodium sulfate. Trace Binding=48%.

EXAMPLE 4

Example 2 was repeated, except second aliquot of coating solution contains 10% ammonium acetate. Trace Binding=30%.

EXAMPLE 5

Purified antiserum specific for thyroxine ($T_4$), (1:4200 titer) was diluted 1:50 in 0.3 M glycine and 0.10 ml aliquots were dispensed into 12×75 mm polystryene test tubes. A second aliquot (0.9 ml) of coating solution containing 22% ammonium sulfate and 2.7% sodium chloride was added sequentially. The mixture was incubated at 4° overnight and aspirated. The tubes were treated with 1.0 ml postcoat solution (0.1% PEG 6000 in 0.01 M, pH 7.4 potassium phosphate). Trace Binding=35%.

EXAMPLE 6

Antiserum specific for insulin diluted 1:5000 in 0.3 M glycine (0.10 ml aliquots) was dispensed into 12×75 mm polystyrene test tubes. A second aliquot (0.9 ml) containing 22% ammonium sulfate and 2.7% sodium chloride was added sequentially. The mixture was incubated for 17 hours at 4, 25 and 37 degrees. The tubes were treated with 1.0 ml postcoat solution (0.1% PEG in 0.01 M, pH 7.4 potassium phosphate). Trace Binding (4° incubation=31%, 25° incubation=30%, 37° incubation=34%).

The present invention is particularly advantageous in that antibodies to lipophilic antigens or haptens can be effectively coated on a solid substrate. The use of a soluble salt to increase the ionic strength of an antibody coating solution unexpectedly provided effective coating of such antibodies in that an increase in ionic strength would have been expected to result in precipitation of the antibody from the solution and/or the formation of antibody aggregates, which would have prevented effective coating.

Numerous modifications and variations of the present invention are possible in light of the above teachings and, therefore, within the scope of the appended claims, the invention may be practised otherwise than as particularly described.

We claim:

1. A process for coating an antibody on a solid substrate, comprising:
   contacting a solid substrate with antibody solution, said antibody being at least one member selected from the group consisting of antibodies to lipophilic haptens and antibodies to lipophilic antigens, said solution having at least one salt dissolved therein to provide a solution having an ionic strength of at least 0.5 and no greater than 10.0; and separating said solution and said solid substrate to provide said solid substrate coated with said antibody.

2. The process of claim 1 wherein the ionic strength of the solution is at least 1.0.

3. The process of claim 1 wherein the salt is at least one member selected from the group consisting of water soluble salts of ammonium, alkali metals and alkaline earth metals.

4. The process of claim 1 wherein said antibody is an antibody to a bile acid.

5. The process of claim 4 wherein the solid substrate is a plastic test tube.

6. The process of claim 4 wherein the antibody solution has an antibody titer of from $1:10^3$ to $1:10^6$.

7. The process of claim 6 wherein the ionic strength is at least 1.0 and no greater than 10.

8. An article suitable for solid phase assay of bile acid, comprising:
   a solid substrate and antibody to bile acid, said antibody being non-covalently coated on the solid substrate.

9. The article of claim 8 wherein the bile acid is conjugated bile acid.

10. A solid substrate non-covalently coated with an antibody to bile acid produced by the process of claim 1.

11. The solid substrate of claim 10 wherein the antibody is to conjugated bile acid.

12. In an assay for a bile acid, the improvement comprising:
   effecting said assay in the solid phase with an article as defined in claim 8.

13. The assay of claim 12 wherein the assay is a radioimmunoassay.

14. The assay of claim 13 wherein the assay is for conjugated bile acid.

15. The assay of claim 14 wherein the assay is effected with cholylglycine histamine $^{125}I$ tracer.

16. In an assay for bile acid, the improvement comprising:
   effecting said assay in the solid phase with an article as defined in claim 10.

17. The assay of claim 16 wherein the assay is a radioimmunoassay.

18. The assay of claim 17 wherein the assay is for conjugated bile acid.

19. The assay of claim 18 wherein the assay is effected with cholylglycine histamine $^{125}I$ tracer.

20. The process of claim 4 wherein the salt is at least one member selected from the group consisting of water soluble salts of ammonium, alkali metals and alkaline earth metals.

21. The process of claim 20 wherein the antibody is an antibody to conjugated bile acid.

22. An article suitable for a solid phase assay produced in accordance with the process of claim 1.

23. The process of claim 1 wherein the antibody is an antibody to bile acid, the solution is buffered to a pH of from 5.0 to 10.0, the antibody titer of the solution is from $1:10^3$ to $1:10^6$, and the ionic strength of the solution is from 0.5 to 10.0.

24. The process of claim 23 wherein the substrate is a polymer.

25. The process of claim 24 wherein the polymer is selected from the group consisting of polystyrene and polypropylene.

26. An article suitable for the solid phase assay of bile acid produced by the process of claim 25.

27. The process of claim 23 wherein the inorganic salt is at least one member selected from the group consisting of ammonium, potassium, and sodium sulfate alone or in admixture with sodium chloride.

28. The process of claim 3 wherein the antibody is an antibody to $T_4$.

29. The process of claim 3 wherein the antibody is an antibody to insulin.

30. The process of claim 1 wherein the ionic strength is no greater than 5.

31. The process of claim 3 wherein the ionic strength is no greater than 5.

* * * * *